United States Patent
Edwards et al.

(10) Patent No.: US 12,378,494 B2
(45) Date of Patent: Aug. 5, 2025

(54) CORROSION INHIBITOR AND INDUSTRIAL LUBRICANT INCLUDING THE SAME

(71) Applicant: Afton Chemical Corporation, Richmond, VA (US)

(72) Inventors: David Edwards, Richmond, VA (US); Helen Ryan, Sheen (GB); Robert Mccovick, Chesterfield, VA (US)

(73) Assignee: Afton Chemical Corporation, Richmond, VA (US)

(*) Notice: Subject to any disclaimer, the term of this patent is extended or adjusted under 35 U.S.C. 154(b) by 0 days.

(21) Appl. No.: 18/505,646

(22) Filed: Nov. 9, 2023

(65) Prior Publication Data
US 2024/0174939 A1 May 30, 2024

Related U.S. Application Data

(60) Provisional application No. 63/424,383, filed on Nov. 10, 2022.

(30) Foreign Application Priority Data

Nov. 29, 2022 (GB) .................................. 2217954

(51) Int. Cl.
*C10M 135/36* (2006.01)
*C07D 285/125* (2006.01)
(Continued)

(52) U.S. Cl.
CPC ....... *C10M 135/36* (2013.01); *C07D 285/125* (2013.01); *C10M 137/12* (2013.01);
(Continued)

(58) Field of Classification Search
CPC .................. C10M 135/36; C10M 137/12; C10M 141/10; C10M 169/04; C10M 2203/003;
(Continued)

(56) References Cited

U.S. PATENT DOCUMENTS 3,087,932 A * 4/1963 Little, Jr. ........... C07D 285/125
548/142
3,533,943 A 10/1970 Papayannopoulos
(Continued)

FOREIGN PATENT DOCUMENTS

CA 1152975 A1 8/1983
CN 1923987 A 3/2007
(Continued)

OTHER PUBLICATIONS

Hipler et al., "N-H•••S hydrogen bonding in 2-mercapto-5-methyl-1,3, 4-thiadiazole. Synthesis and crystal structures of mercapto functionalised 1,3,4-thiadiazoles", Molecular Structure, May 8, 2003, 13 pages.
(Continued)

*Primary Examiner* — Ellen M McAvoy
(74) *Attorney, Agent, or Firm* — Honigman LLP

(57) ABSTRACT

Disclosed herein are corrosion inhibitors suitable for heavy-duty industrial lubricants and industrial lubricating compositions including such corrosion inhibitors combined with phosphonate diesters to provide good copper corrosion and roller bearing protection. The corrosion inhibitor has a high content of dialkyl dithiothiadiazole compounds configured to maintain high levels of the phosphonate diester in the lubricant.

21 Claims, 1 Drawing Sheet

Figure 1:
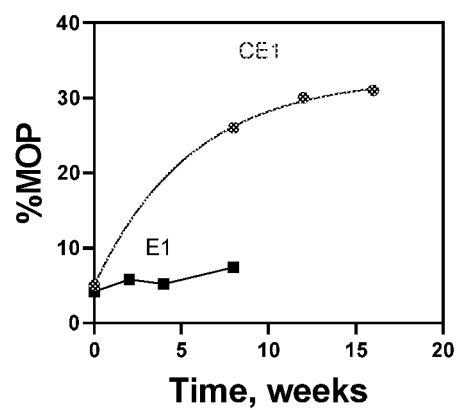

(51) Int. Cl.
  *C10M 137/12* (2006.01)
  *C10M 141/10* (2006.01)
  *C10M 169/04* (2006.01)
  *C10N 30/12* (2006.01)
  *C10N 40/02* (2006.01)

(52) U.S. Cl.
  CPC ........ *C10M 141/10* (2013.01); *C10M 169/04* (2013.01); *C10M 2203/003* (2013.01); *C10M 2219/106* (2013.01); *C10M 2223/06* (2013.01); *C10N 2030/12* (2013.01); *C10N 2040/02* (2013.01)

(58) Field of Classification Search
  CPC ........ C10M 2219/106; C10M 2223/06; C07D 285/125; C10N 2030/12; C10N 2040/02
  USPC .......................................................... 508/273
  See application file for complete search history.

(56) References Cited

U.S. PATENT DOCUMENTS

| | | | |
|---|---|---|---|
| 3,882,031 | A | 5/1975 | Askew et al. |
| 4,260,501 | A | 4/1981 | Shim |
| 4,298,481 | A | 11/1981 | Clarke |
| 4,410,436 | A | 10/1983 | Holstedt et al. |
| 4,719,001 | A | 1/1988 | Dvoracek |
| 5,094,763 | A | 3/1992 | Tochigi et al. |
| 5,302,304 | A | 4/1994 | Valcho |
| 5,585,338 | A | 12/1996 | Beltzer |
| 5,656,577 | A | 8/1997 | Kato |
| 5,801,130 | A | 9/1998 | Francisco |
| 7,759,294 | B2 | 7/2010 | Devlin et al. |
| 7,786,059 | B2 | 8/2010 | Buitrago |
| 7,820,602 | B2 | 10/2010 | Ravichandran et al. |
| 7,851,418 | B2 | 12/2010 | Habeeb et al. |
| 8,080,500 | B2 | 12/2011 | Ravichandran et al. |
| 8,410,032 | B1* | 4/2013 | Carroll ................. C10M 141/08 508/293 |
| 9,150,812 | B2 | 10/2015 | Cooper et al. |
| 9,296,973 | B2 | 3/2016 | Fu et al. |
| 9,404,059 | B2 | 8/2016 | Tsujimoto et al. |
| 9,540,582 | B2 | 1/2017 | Barton et al. |
| 10,808,198 | B2 | 10/2020 | Fang |
| 11,214,755 | B2 | 1/2022 | Susukida et al. |
| 2002/0151443 | A1 | 10/2002 | Srinivasan |
| 2005/0261141 | A1 | 11/2005 | Iso et al. |
| 2006/0025314 | A1 | 2/2006 | Henly |
| 2008/0058235 | A1 | 3/2008 | Takigawa |
| 2008/0194442 | A1 | 8/2008 | Watts et al. |
| 2009/0093384 | A1 | 4/2009 | Ward et al. |
| 2009/0318319 | A1 | 12/2009 | Devlin et al. |
| 2010/0016189 | A1 | 1/2010 | Baker |
| 2010/0130390 | A1* | 5/2010 | Tipton ................. C10M 141/10 508/273 |
| 2011/0004001 | A1* | 1/2011 | Coucharriere ..... C07D 285/125 548/142 |
| 2014/0038864 | A1 | 2/2014 | Shough et al. |
| 2015/0072908 | A1* | 3/2015 | Tsujimoto ............ C10M 141/10 508/330 |
| 2015/0218481 | A1* | 8/2015 | Bouffet ................. C10M 161/00 508/273 |
| 2016/0168505 | A1 | 6/2016 | Bouvier et al. |
| 2018/0142181 | A1* | 5/2018 | Chen .................... C10M 141/08 |
| 2022/0380326 | A1* | 12/2022 | Adams ................. C07D 417/12 |

FOREIGN PATENT DOCUMENTS

| | | |
|---|---|---|
| CN | 1940037 A | 4/2007 |
| CN | 1940040 A | 4/2007 |
| CN | 101857580 A | 10/2010 |
| CN | 101830865 B | 5/2012 |
| CN | 103509636 A | 1/2014 |
| CN | 104087390 A | 10/2014 |
| CN | 104725740 A | 6/2015 |
| CN | 107034001 A | 8/2017 |
| CN | 108251196 A | 7/2018 |
| CN | 109574957 A | 4/2019 |
| EP | 45827 B1 | 11/1983 |
| EP | 0210366 A | 2/1987 |
| EP | 310364 A1 | 4/1989 |
| EP | 0310366 A1 | 4/1989 |
| EP | 0391649 A2 | 10/1990 |
| EP | 0280580 A2 | 11/1992 |
| EP | 0524452 A1 | 1/1993 |
| EP | 1191087 A1 | 3/2002 |
| EP | 1239021 A2 | 9/2002 |
| EP | 1308496 B1 | 6/2006 |
| EP | 1918356 A4 | 12/2008 |
| EP | 2546324 A1 | 1/2013 |
| EP | 2829591 A4 | 11/2015 |
| EP | 2829592 A4 | 11/2015 |
| EP | 2027236 B1 | 6/2016 |
| EP | 2546324 B1 | 4/2021 |
| GB | 1440129 A | 6/1976 |
| JP | 08165483 A | 6/1996 |
| JP | 3005310 B2 | 1/2000 |
| JP | 6158567 B2 | 7/2017 |
| JP | 2020041055 A | 3/2020 |
| JP | 2021066809 A | 4/2021 |
| JP | 2021080339 A | 5/2021 |
| JP | 2021080429 A | 5/2021 |
| KR | 1715372 B1 | 3/2017 |
| WO | 8803551 A1 | 5/1988 |
| WO | 20090111235 A2 | 9/2009 |
| WO | 20100141003 A1 | 12/2010 |
| WO | 20120112635 A1 | 8/2012 |
| WO | 2023022930 A1 | 8/2022 |
| WO | 2023022931 A1 | 2/2023 |

OTHER PUBLICATIONS

European Search Report issued in Application No. 23207147.2 mailed Mar. 11, 2024, 8 pages.
Liu, Hongli; et al., "Synthesis of a terpolymer containing fluorene, side chain conjugated thiophene and benzothiadiazole and its applications in photovoltaic devices", Journal of Applied Polymer Science (2013), 128(5), 3250-3255 (Abstract).
Wu, Xianli; et al., "Synthesis and characterization of α-aminophosphonates containing 1,3,4-thiadiazole", Youji Huaxue (2009), 29(9), 1429-1433 (Abstract).
Lu, Shui-Ming; et al., "Synthesis of α-aminophosphonate derivatives of 1,3,4-thiadiazole and their biological activities", Hecheng Huaxue (1999), 7(3), 270-274 (Abstract).
Lu, Shui-Ming; et al., "A convenient and facile synthesis of O,O-diphenyl 1-(5-alkyl-1,3,4-thiadiazol-2-yl)amino-1-arylmethylphosphonates", Synthetic Communications (1999), 29(19), 3443-3450 (Abstract).
Sidky, M. M.; et al., "Alkyl phosphites and phosphonates as alkylating agents for 1,3,4-thiadiazolidine-2,5-dithiones", Organic Preparations and Procedures International (1982), 14(4), 225-32 (Abstract).
Combined Search and Examination Report under Sections 17 and 18(3) for GB2217954.3 dated Jan. 20, 2023.
Extended European Search Report for EP 23207147.2 dated Mar. 11, 2024.
Hipler et al., "N-H•••S hydrogen bonding in 2-mercapto-5-methyl-1,3, 4-thiadiazole. Synthesis and crystal structures of mercapto functionalised 1,3,4-thiadiazoles" Journal Of Molecular Structure, v 658, n 3, Oct. 1, 2003, pp. 179-191.

\* cited by examiner

CORROSION INHIBITOR AND INDUSTRIAL LUBRICANT INCLUDING THE SAME

CROSS-REFERENCE TO RELATED APPLICATION

This Application claims the benefit of U.S. Provisional Application No. 63/424,383 filed on Nov. 10, 2022. This Application also claims the benefit of GB 2217954.3 filed on Nov. 29, 2022. The entire contents of both applications are incorporated herein by reference in their entirety.

TECHNICAL FIELD

The present disclosure relates to corrosion inhibitors suitable for heavy duty or industrial lubricants achieving good wear performance, low copper corrosion, and/or low roller bearing weight loss.

BACKGROUND

Driveline hardware like gears, axles, and the like commonly require lubricants that provide antiwear or extreme pressure protection. In practice, gears and axles can be operated at full-load capacity and/or with frequent stop-and-go operations putting additional stress and strain on the hardware. Thus, lubricants for heavy duty gear and axle applications need additive chemistry to reliably protect gears and axles under both the full-load and the stop-and-go operating conditions.

Typically, lubricants for such heavy-duty applications require, for example, the fluid to meet one or more performance characteristics of extreme pressure, antiwear, friction, and/or copper corrosion to suggest but a few of the common requirements of driveline hardware fluids. A number of additives may be included in the lubricant to achieve such performance. For instance, lubricants often include sulfurized additives, such as a thiadiazole compound, to protect gears and other components from corrosion and wear. Typically, these lubricants will also have a phosphorus compound to act as either an antiwear additive or a friction modifier. One means of determining the antiwear capacity of a gear lubricant is to run a FE8 bearing test according to DIN 51819-3 (80 hours, 7.5 rpm, 100 kN, and 80° C.). Phosphonate diesters, and in particular dimethyl octadecyl phosphonate, are known to provide bearing protection in the FE8 bearing test. Unfortunately, thiadiazole corrosion inhibitors, when used in combination with phosphonate diesters, tend to interact with the diester and can degrade the diester to a monoester form. Monoester variants of phosphonates, however, are not as effective in protecting against roller bearing wear. Thus there is a need to modify thiadiazole corrosion inhibitors in a way that both preserves their effect as a corrosion inhibitor while allowing phosphonate diesters to play their role as an antiwear additive or friction modifier.

SUMMARY

In one approach or embodiment, a corrosion inhibitor is described herein made by a process comprising (a) reacting a 1,3,4-dimercapto thiadiazole or alkali metal salt thereof with an alkyl mercaptan in the presence of an acid to form a first reaction intermediate; (b) reacting the first reaction intermediate with hydrogen peroxide to form the corrosion inhibitor; and (c) wherein the 1,3,4-dimercapto thiadiazole or alkali metal salt thereof, the alkyl mercaptan, and the hydrogen peroxide are provided at a molar ratio of 1:1.95-2.15:greater than 2.0.

In other approaches or embodiments, the corrosion inhibitor of the previous paragraph may be combined with optional features or embodiments in any combination. These optional features or embodiments may include one or more of the following: wherein the acid is a strong acid provided in molar excess to the 1,3,4-dimercapto thiadiazole; and/or wherein the corrosion inhibitor is about 95 weight percent or more of a 2,5-dialkyl-dithiothiadiazole compound and about 5 weight percent or less of a monoalkyl-dithiothiadiazole compound; and/or wherein the corrosion inhibitor has a total acid number of 10 or less; and/or wherein the process further includes heating the corrosion inhibitor to a temperature effective to separate any aqueous layer and optionally subjecting the heated corrosion inhibitor to a vacuum strip; and/or wherein the 2,5-dialkyl-dithiothiadiazole compound has the structure of Formula Ia:

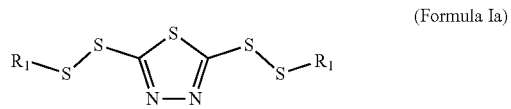

(Formula Ia)

and
wherein the monoalkyl dithiothiadiazole compound has the structure of Formula Ib:

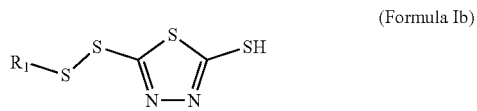

(Formula Ib)

wherein each $R_1$ of Formula Ia and/or Formula Ib is independently a linear or branched C4 to C20 hydrocarbyl group; and/or wherein the alkyl moiety of the alkyl mercaptan is an aliphatic or aromatic hydrocarbyl group; and/or wherein the alkyl moiety of the alkyl mercaptan is a linear or branched C1 to C30 hydrocarbyl group; and/or wherein the dimercapto thiadiazole or alkali metal salt thereof, the alkyl mercaptan, and the hydrogen peroxide are provided at a molar ratio of 1:1.95-2.15:2.1-2.4.

In another approach or embodiment, a lubricant is described herein comprising: (a) a majority of base oil; and (b) a corrosion inhibitor made by a process comprising: (i) reacting a 1,3,4-dimercapto thiadiazole or alkali metal salt thereof with an alkyl mercaptan in the presence of an acid to form a first reaction intermediate; (ii) reacting the first reaction intermediate with hydrogen peroxide to form the corrosion inhibitor; and (iii) wherein the 1,3,4-dimercapto thiadiazole or alkali metal salt thereof, the alkyl mercaptan, and the hydrogen peroxide are provided at a molar ratio of 1:1.95-2.15:greater than 2.0.

In other approaches or embodiments, the lubricant of the previous paragraph may be combined with optional features or embodiments in any combination. These optional features or embodiments may include one or more of the following: wherein the acid is a strong acid provided in molar excess to the 1,3,4-dimercapto thiadiazole; and/or further comprising one or more phosphonate ester compounds including, based on the total weight percent of phosphonate ester compounds, about 90 weight percent or more of a phosphonate diester and no more than about 10 weight percent of a phosphonate monoester; and/or wherein the corrosion inhibitor is about 95 weight percent or more of a 2,5-dialkyl-dithiothiadiazole compound and about 5 weight percent or less of a monoalkyl-dithiothiadiazole compound; and/or wherein the 2,5-dialkyl-dithiothiadiazole compound has the structure of Formula Ia:

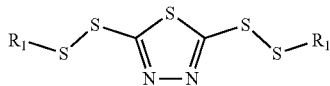
(Formula Ia)

and
wherein the monoalkyl-dithiothiadiazole compound has the structure of Formula Ib:

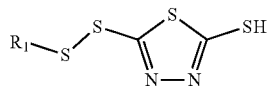
(Formula Ib)

wherein each $R_1$ of Formula Ia and/or Formula Ib is, independently, a linear or branched C4 to C20 hydrocarbyl group; and/or wherein the phosphonate diester has a structure of Formula II

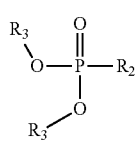
(Formula II)

wherein $R_2$ is a C1 to C50 hydrocarbyl group and each $R_3$ is, independently, a C1 to C20 alkyl group; and/or wherein the phosphonate diester is dimethyl octadecyl phosphonate (DMOP);
and/or wherein the phosphonate monoester has a structure of Formula III

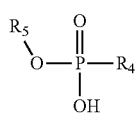
(Formula III)

wherein $R_4$ is a C1 to C50 hydrocarbyl group and $R_5$ is a C1 to C20 alkyl group; and/or wherein the phosphonate monoester is methyl octadecyl phosphonate (MOP); and/or wherein the process further includes heating the corrosion inhibitor to a temperature effective to separate any aqueous layer and optionally subjecting the heated corrosion inhibitor to a vacuum strip; and/or wherein the lubricant exhibits a FAG FE8 roller bearing weight loss of about 12 mg of less pursuant to DIN 51819-3 after 80 hours of runtime at 80° C., 7.5 rpm, and 100 kN.

In yet further approaches or embodiments, a corrosion inhibitor additive is described herein comprising: (a) about 95 weight percent or more of a 2,5-dialkyl-dithiothiadiazole compound; (b) a monoalkyl-dithiothiadiazole compound, but no more than about 5 weight percent of the monoalkyl-dithiothiadaizole compound; and (c) wherein the total acid number of the corrosion inhibitor additive is about 10 or less.

In other approaches or embodiments, the corrosion inhibitor additive of the previous paragraph may be combined with optional features or embodiments in any combination. These optional features or embodiments may include one or more of the following: wherein the 2,5-dialkyl-dithiothiadiazole compound has the structure of Formula Ia:

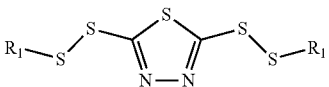
(Formula Ia)

and
wherein the monoalkyl-dithiothiadiazole compound has the structure of Formula Ib:

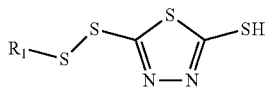
(Formula Ib)

wherein each $R_1$ of Formula Ia and/or Formula Ib is independently a linear or branched C4 to C20 hydrocarbyl group; and/or wherein the corrosion inhibitor is obtained from a dimercapto thiadiazole or alkali metal salt thereof, an alkyl mercaptan, and a hydrogen peroxide provided at a molar ratio of 1:1.95-2.15:2.1-2.4.

In yet further approaches or embodiments, the use of any embodiment of the corrosion inhibitor or lubricant of this Summary is described for achieving a passing FAG FE8 roller bearing weight loss of about 12 mg or less pursuant to DIN 51819-3 after 80 hours of runtime at 80° C., 7.5 rpm, and 100 kN Other embodiments of the present disclosure will be apparent to those skilled in the art from consideration of the specification and practice of the invention disclosed herein. The following definitions of terms are provided in order to clarify the meanings of certain terms as used herein.

The terms "gear oil," "gear fluid," "gear lubricant," "base gear lubricant," "lubricating oil," "lubricant composition," "lubricating composition," "lubricant" and "lubricating fluid" refer to a finished lubrication product comprising a major amount of a base oil plus a minor amount of an additive composition as discussed herein. Such gear fluids are for use in extreme pressure situations such as for transmissions and gear drive components having metal-on-metal contact situations, for instance, in a transmission (manual or automatic) and/or a gear differential.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having a predominantly hydrocarbon character. Each hydrocarbyl group is independently selected from hydrocarbon substituents, and substituted hydrocarbon substituents containing one or more of halo groups, hydroxyl groups, alkoxy groups, mercapto groups, nitro groups, nitroso groups, amino groups, pyridyl groups, furyl groups, imidazolyl groups, oxygen and nitrogen, and wherein no more than two non-hydrocarbon substituents are present for every ten carbon atoms in the hydrocarbyl group.

As used herein, the term "percent by weight" or "wt %" or "weight percent", unless expressly stated otherwise, means the percentage the recited component represents to the weight of the entire composition. All percent numbers herein, unless specified otherwise, is weight percent.

The terms "soluble," "oil-soluble," or "dispersible" used herein may, but does not necessarily, indicate that the compounds or additives are soluble, dissolvable, miscible, or capable of being suspended in the oil in all proportions. The foregoing terms do mean, however, that they are, for instance, soluble, suspendable, dissolvable, or stably dispersible in oil to an extent sufficient to exert their intended effect in the environment in which the oil is employed. Moreover, the additional incorporation of other additives may also permit incorporation of higher levels of a particular additive, if desired.

The term "alkyl" as employed herein refers to straight, branched, cyclic, and/or substituted saturated chain moieties from about 1 to about 200 carbon atoms. The term "alkenyl" as employed herein refers to straight, branched, cyclic, and/or substituted unsaturated chain moieties from about 3 to about 30 carbon atoms. The term "aryl" as employed herein refers to single and multi-ring aromatic compounds that may include alkyl, alkenyl, alkylaryl, amino, hydroxyl, alkoxy, halo substituents, and/or heteroatoms including, but not limited to, nitrogen, and oxygen.

As used herein, the molecular weight is determined by gel permeation chromatography (GPC) using commercially available polystyrene standards (with a Mn of about 180 to about 18,000 as the calibration reference). The molecular weight (Mn) for any embodiment herein may be determined with a gel permeation chromatography (GPC) instrument obtained from Waters or the like instrument and the data processed with Waters Empower Software or the like software. The GPC instrument may be equipped with a Waters Separations Module and Waters Refractive Index detector (or the like optional equipment). The GPC operating conditions may include a guard column, 4 Agilent PLgel columns (length of 300×7.5 mm; particle size of 5μ, and pore size ranging from 100-10000 Å) with the column temperature at about 40° C. Un-stabilized HPLC grade tetrahydrofuran (THF) may be used as solvent, at a flow rate of 1.0 mL/min. The GPC instrument may be calibrated with commercially available polystyrene (PS) standards having a narrow molecular weight distribution ranging from 500-380,000 g/mol. The calibration curve can be extrapolated for samples having a mass less than 500 g/mol. Samples and PS standards can be in dissolved in THF and prepared at concentration of 0.1-0.5 weight percent and used without filtration. GPC measurements are also described in U.S. Pat. No. 5,266,223, which is incorporated herein by reference. The GPC method additionally provides molecular weight distribution information; see, for example, W. W. Yau, J. J. Kirkland and D. D. Bly, "Modern Size Exclusion Liquid Chromatography", John Wiley and Sons, New York, 1979, also incorporated herein by reference.

It is to be understood that throughout the present disclosure, the terms "comprises," "includes," "contains," etc. are considered open-ended and include any element, step, or ingredient not explicitly listed. The phrase "consists essentially of" is meant to include any expressly listed element, step, or ingredient and any additional elements, steps, or ingredients that do not materially affect the basic and novel aspects of the invention. The present disclosure also contemplates that any composition described using the terms, "comprises," "includes," "contains," is also to be interpreted as including a disclosure of the same composition "consisting essentially of" or "consisting of" the specifically listed components thereof.

BRIEF DESCRIPTION OF DRAWING FIGURES

Figure 2:
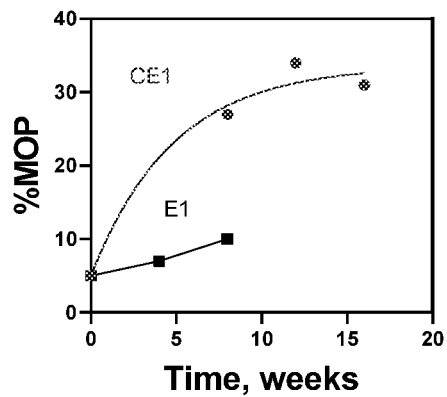

FIG. 1 is a graph of weight percent MOP in a comparative and inventive industrial lubricant subjected to aging at about 40° C.; and FIG. 2 is a graph of weight percent MOP in a comparative and inventive industrial lubricant aged at about 55° C.

DETAILED DESCRIPTION

In one approach or embodiment, disclosed herein are corrosion inhibitors suitable for heavy-duty and/or industrial lubricants and industrial lubricating compositions including such corrosion inhibitors. In some embodiments, the industrial lubricating compositions herein include unique corrosion inhibitors combined with one or more phosphonate diesters to provide good copper corrosion and roller bearing protection at the same time. The corrosion inhibitors and lubricants including such corrosion inhibitors are suitable for use as industrial gear oils for transmission fluids (i.e., manual, automatic, or dual-clutch transmissions), gear fluids, axle fluids, differential fluids, and/or lubricating fluids for other gear-type applications configured for heavy-duty use such as turbines, wind turbines, and the like.

In one aspect of the present disclosure, a corrosion inhibitor is made by a unique process with select molar ratios of a dimercapto thiadiazole or alkali metal salt thereof, an alkyl mercaptan, and a hydrogen peroxide to form a corrosion inhibitor maximizing a dialkyl-dithiothiadiazole content. In other approaches or embodiments, the corrosion inhibitor has a maximized amount of the dialkyl thiadiazole compound with about 95 weight percent or more of a 2,5-dialkyl-dithiothiadiazole compound and about 5 weight percent or less of a monoalkyl-dithiothiadiazole compound.

In yet further approaches or embodiments, the corrosion inhibitor includes a mixture of dialkyl and monoalkyl dithiothiadiazole compounds with about 95 weight percent or more of the dialkyl-dithiothiadiazole compounds and about 5 weight percent or less of the monoalkyl-dithio-thiadiazole compounds. Such corrosion inhibitor is suitable for use in lubricants including one or more phosphonate diesters and configured to maintain high levels of the diester. In approaches, lubricants herein with the phosphonate diester and the unique corrosion inhibitor also have a weight ratio of phosphonate diester-to-phosphonate monoester of about 90:10 to 98:2 for at least about 8 weeks at 25° C., 40° C., or 50° C.

Corrosion Inhibitor

In approaches or embodiments, the corrosion inhibitor is a thiadiazole compound or derivative thereof and, in particular, a mixture of thiadiazole compounds and/or hydrocarbyl-substituted derivatives thereof made by a particular process configured to maximize the content of dialkyl-dithiothiadiazole compounds or derivatives thereof in the mixture and to minimize the content of any monoalkyl-dithiothiadiazole and/or other bis-thiadiazole contaminants in the mixture.

More specifically, the methods herein are configured to maximize the content of dialkyl-dithiothiadiazole compounds or derivatives thereof of Formula Ia in a corrosion inhibitor mixture and to minimize the monoalkyl dithiothiadiazole compounds of Formula Ib in the mixture. In approaches, the dialkyl-dithiothiadiazole compound has the structure of Formula 1a:

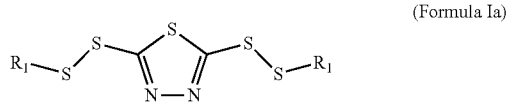
(Formula Ia)

and the monoalkyl-dithiothiadiazole compound has the structure of Formula Ib:

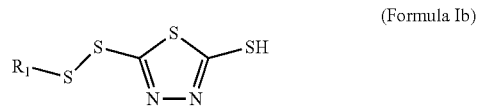
(Formula Ib)

wherein each $R_1$ of Formula Ia and/or Formula Ib is, independently, a linear or branched C4 to C20 hydrocarbyl group and, preferably, a linear or branched C10 to C16 hydrocarbyl group.

The methods herein are configured to produce a mixture of such thiadiazole compounds or derivative thereof including the blend of compounds having the structures of Formula Ia and Ib with compounds of Formula Ia being maximized in the blend. In other approaches, the corrosion inhibitor is a blend of compound Ia and Ib with about 95 weight percent or more of compounds of Formula Ia (preferably about 95 to about 99.5 weight percent) and about 5 weight percent or less of compounds of Formula Ib (preferably about 0.05 to about 5 weight percent). In another approach, the corrosion inhibitor is a mixture of 2,5 dimercapto 1,3,4 thiadiazole compounds including a blend of 2,5-bis-(nonyldithio)-1,3,4-thiadiazole (such as about 95 weight percent or more or about 95 weight percent to about 99.5 weight percent) and 2,5-mono-(nonyldithio)-1,3,4-thiadiazole (such as about 5 weight percent or less or about 0.05 weight percent to about 5 weight percent).

The corrosion inhibitors herein are prepared in a specific reaction having a very tightly controlled molar ratio of a (i) 1,3,4-dimercapto thiadiazole or alkli metal salt thereof, (ii) an alkyl mercaptan, and (iii) a hydrogen peroxide. In approaches or embodiments, the novel corrosion inhibitors herein are made by a process comprising (a) reacting a 1,3,4-dimercapto thiadiazole or alkali metal salt thereof with an alkyl mercaptan in the presence of an acid to form a first reaction intermediate; (b) reacting the first reaction intermediate with hydrogen peroxide to form the corrosion inhibitor; and (c) wherein the dimercapto thiadiazole or alkali metal salt thereof, the alkyl mercaptan, and the hydrogen peroxide are provided in specific molar ratios including 1.95 to 2.15 molar equivalents of the alkyl mercaptan relative to the thiadiazole and also greater than 2.0 molar equivalents of the hydrogen peroxide to the thiadiazole, and preferably, 2.1 to 2.4 molar equivalents of the hydrogen peroxide to the thiadiazole. Such tightly controlled molar ratios of reactants are configured to maximize the dialkyl-dithiothiadiazole content in the resulting mixture. Overall, the 1,3,4-dimercapto thiadiazole or alkali metal salt thereof, the alkyl mercaptan, and the hydrogen peroxide are provided at a molar ratio of 1:1.95-2.15:greater than 2.0, and preferably, a molar ratio of 1:1.95-2.15:2.1-2.4.

In approaches, the methods herein first react 1,3,4-dimercapto thiadiazole or an alkali metal salt thereof with an alkyl mercaptan in the presence of an optional solvent and/or acid at a temperature of about 0° C. to about 100° C., preferably, about 15° C. to about 85° C., and more preferably, about 70° C. to about 85° C. to form first reaction intermediate. If an alkali metal salt of the dimercapto thiadiazole is used (such as sodium salt of 2,5-dimercapto-1,3,4-thiadiazole, or for instance, sodium 2,5-dimercapto-1, 3,4-thiadiazole), then sufficient amounts of an inorganic acid may be used such as, for example, sulfuric acid, nitric acid, hydrochloric acid, phosphoric acid, hydrobromic acid, perchloric acid, hydroiodic acid, p-toluenesulfonic acid, and/or methanesulfonic acid, and the like. Preferably, the acid is a strong acid provided in a molar excess to the 1,3,4-dimercapto thiadiazole. As used herein, a strong acid reference to one that is completely dissociated or ionized in an aqueous solution. Preferably, the acid is sulfuric acid. Next, the first reaction intermediate may be further reacted with hydrogen peroxide to form the corrosion inhibitor herein. The hydrogen peroxide and inorganic acid, if used, are added slowly in their respective steps and it may be preferred to add the hydrogen peroxide over a period of about 3 or more hours, preferably about 3 to about 6 hours, and more preferably, about 3 to about 4 hours. After addition of the hydrogen peroxide, it may be advantageous to maintain the resulting reaction mixture at a temperature in the above-noted range and/or increase the temperature to above 85° C. and, preferably about 88° C. to about 100° C. for a short period of time to finalize the reaction product of the first reaction step. The organic layer may then be optionally washed with water and/or optionally stripped of solvent to produce the first reaction product mixture from this first reaction step.

Suitable alkyl mercaptans have the general formula R—SH wherein R can be aliphatic or aromatic hydrocarbyl group including, but not limited to, acyclic, alicyclic, aralkyl, aryl, and alkaryl radicals or mixtures of such radicals. The hydrocarbyl group may include from 1 to 30 carbons and, preferably, are linear or branched alkyl groups containing from 4 to 16 carbons. Examples of suitable alkyl mercaptans may be, but not limited to, ethyl mercaptan, propyl mercaptan, butyl mercaptan, hexyl mercaptan, octyl mercaptan, nonyl mercaptan, dodecyl mercaptan, tridecyl mercaptan, hexadecyl mercaptan, octadecyl mercaptan, cyclohexyl mercaptan, phenyl mercaptan, tolyl mercaptan, benzyl mercaptan, naphthyl mercaptan, styryl mercaptan, and the like, and mixtures thereof. In one approach, a preferred alkyl mercaptan is tert-nonyl mercaptan.

If needed, the reaction step may occur in the presence of an optional solvent. The solvent may be any suitable solvent chemically inert with hydrogen peroxide. The solvent may be refluxed during the reaction and, if needed, may assist in controlling the reaction temperature. Suitable solvents may be water, methanol, acetone, phenol, isopropanol, ethanol, pentanol, ethylene glycol, glycerol, erythritol, and the like, or mixtures thereof.

Inorganic acids may also be used in the reaction and suitable inorganic acids are those acids that will readily react with sodium or other alkali metal substituents to form a water soluble salt. Such acids include, but are not limited to, sulfuric acid, phosphoric acid, sulfurous acid, phosphorous acid, hydrochloric acid, hydrofluoric acid, and the like, and combinations thereof. In one approach, sulfuric acid is preferred.

In some approaches or embodiments, the methods herein further including heating the thiadiazole corrosion inhibitor to a temperature effective to separate any aqueous layer and optionally subjecting the heated thiadiazole corrosion inhibitor from step to a vacuum strip. Heating may be to a temperature of about 100° C. to about 110° C. under vacuum for up to 1 to 2 hours as needed to form the final corrosion inhibitors herein.

In some approaches, the formed corrosion inhibitor additive includes (a) about 95 weight percent or more of a 2,5-dialkyl-dithiothiadiazole compound; (b) a monoalkyl-dithiothiadiazole compound, but no more than about 5 weight percent of the monoalkyl-dithiothiadaizole; and (c) wherein the total acid number of the corrosion inhibitor is about 10 or less. In some embodiments, the corrosion inhibitor is obtained from a 1,3,4-dimercapto thiadiazole or alkali metal salt thereof, an alkyl mercaptan, and a hydrogen peroxide provided at a molar ratio of 1:1.95 to 2.15:2.1 to 2.4.

Suitable treat rates of the corrosion inhibitor in the lubricants of this disclosure may be about 0.1 to about 1.0 weight percent, preferably about 0.2 to about 0.6 weight percent, and more preferably about 0.2 to about 0.4 weight percent.

Phosphonate Diester

Industrial or heavy duty lubricating oil compositions herein may further include low amounts of phosphonate diesters to provide, among other features, improved roller bearing wear protection. If included, the compositions may include less than about 0.5 weight percent, in other approaches, less than about 0.4 weight percent, in further approaches, less than about 0.3 percent, and in yet further approaches, about 0.25 percent or less of the phosphonate diesters. In other approaches, the compositions herein may include about 0.05 weight percent or more, or about 0.1 weight percent or more, or about 0.15 weight percent or more of the phosphonate diester. In embodiments herein, lubricating oil compositions including the corrosion inhibitor discussed above maintain high levels of the phosphonate diester during aging and, as shown in the Examples below, maintain about 10 weight percent or less of monoester phosphonates.

In some approaches, the phosphonate diesters may have a structure of Formula II

(Formula II)

wherein $R_2$ is a C1 to C50 hydrocarbyl chain (preferably a C1 to C30, more preferably a C10 to C20 hydrocarbyl chain) and each $R_3$ is, independently, a C1 to C20 alkyl group, a C1 to C10 alkyl group or, preferably, a C1 to C4 alkyl group.

Suitable phosphonate diesters may include O,O-di-(primary alkyl)acyclic hydrocarbyl phosphonates in which the primary alkyl groups are the same or different and each independently containing 1 to 4 carbon atoms and in which the acyclic hydrocarbyl group bonded to the phosphorus atom may contain 12 to 30 carbon atoms and is a linear hydrocarbyl group free of acetylenic unsaturation. Exemplary compounds include O,O-dimethyl hydrocarbyl phosphonates, O,O-diethyl hydrocarbyl phosphonates, O,O-dipropyl hydrocarbyl phosphonates, O,O-dibutyl hydrocarbyl phosphonates, O,O-diiso-butyl hydrocarbyl phosphonates, and analogous compounds in which the two alkyl groups differ, such as, for example, O-ethyl-O-methyl hydrocarbyl phosphonates, O-butyl-O-propyl hydrocarbyl phosphonates, and O-butyl-O-isobutyl hydrocarbyl phosphonates, wherein in each case the hydrocarbyl group is linear and is saturated or contains one or more olefinic double bonds, each double bond preferably being an internal double bond. Suitable compounds include compounds in which both O,O-alkyl groups are identical to each other. Other suitable compounds include compounds in which the hydrocarbyl group bonded to the phosphorus atom contains 16 to 20 carbon atoms. A particularly suitable hydrocarbyl phosphonate diester is dimethyl octadecyl phosphonate. Other examples of suitable phosphonate diesters include, but are not limited to, dimethyl triacontyl phosphonate, dimethyl triacontenyl phosphonate, dimethyl eicosyl phosphonate, dimethyl hexadecyl phosphonate, dimethyl hexadecenyl phosphonate, dimethyl tetracontenyl phosphonate, dimethyl hexacontyl phosphonate, dimethyl dodecyl phosphonate, dimethyl dodecenyl phosphonate and the like.

Base Oil

In one approach, suitable base oils for use in the lubricating composition or gear fluids herein include mineral oils, synthetic oils, and include all common mineral oil basestocks. The mineral oil may be naphthenic or paraffinic. Viscosities of the heavy-duty or industrial gear oils herein may range from a KV100 (ASTM 445) of about 5 cSt to about 50 cSt, or about 10 cSt to about 40 cSt, or about 20 cSt to about 40 cSt. The mineral oil may be refined by conventional methodology using acid, alkali, and clay or other agents such as aluminium chloride, or may be an extracted oil produced, e.g. by solvent extraction with solvents such as phenol, sulfur dioxide, furfural or dichlorodiethyl ether. The mineral oil may be hydrotreated or hydrofined, dewaxed by chilling or catalytic dewaxing processes, or hydrocracked, such as the Yubase® family of hydrockracked base oils from SK Innovation Co., Ltd. (Seoul, Korea). The mineral oil may be produced from natural crude sources or be composed of isomerized wax materials or residues of other refining processes.

The base oil or base oil of lubricating viscosity used in the compositions herein may be selected from any suitable base oil for driveline or gear oil applications. Examples include the base oils in Groups I-V as specified in the American Petroleum Institute (API) Base Oil Interchangeability Guidelines. These three base oil groups are as follows:

TABLE 1

| Base Oil Types | | | | |
|---|---|---|---|---|
| Base Oil Category | Sulfur (%) | | Saturates (%) | Viscosity Index |
| Group I | >0.03 | and/or | <90 | 80 to 120 |
| Group II | ≤0.03 | and | ≥90 | 80 to 120 |
| Group III | ≤0.03 | and | ≥90 | ≥120 |
| Group IV | All polyalphaolefins (PAOs) | | | |
| Group V | All others not included in Groups I, II, III, or IV | | | |

Groups I, II, and III are mineral oil process stocks and may be preferred for the driveline or gear fluids of the present application. It should be noted that although Group III base oils are derived from mineral oil, the rigorous processing that these fluids undergo causes their physical properties to be very similar to some true synthetics, such as PAOs. Therefore, oils derived from Group III base oils may be referred to as synthetic fluids in the industry. Suitable oils may be derived from hydrocracking, hydrogenation, hydrofinishing, unrefined, refined, and re-refined oils, and mixtures thereof. In some approaches, the base oil may be a blend of Group I and Group II oils and the blend may be about 0% to about 100% of the Group I oil, about 0% to about 100% of the Group II oil, about 0% to about 100% of the Group III oil, or various blends of Group I and II, Group I and III, or Group II and III oil blends.

Unrefined oils are those derived from a natural, mineral, or synthetic source without or with little further purification treatment. Refined oils are similar to the unrefined oils except that they have been treated in one or more purification steps, which may result in the improvement of one or more properties. Examples of suitable purification techniques are solvent extraction, secondary distillation, acid or base extraction, filtration, percolation, and the like. Oils refined to the quality of an edible may or may not be useful. Edible oils may also be called white oils. In some embodiments, lubricating oil compositions are free of edible or white oils.

Re-refined oils are also known as reclaimed or reprocessed oils. These oils are obtained similarly to refined oils using the same or similar processes. Often these oils are additionally processed by techniques directed to removal of spent additives and oil breakdown products.

Mineral oils may include oils obtained by drilling or from plants and animals or any mixtures thereof. For example such oils may include, but are not limited to, castor oil, lard oil, olive oil, peanut oil, corn oil, soybean oil, and linseed oil, as well as mineral lubricating oils, such as liquid petroleum oils and solvent-treated or acid-treated mineral lubricating oils of the paraffinic, naphthenic or mixed paraffinic-naphthenic types. Such oils may be partially or fully hydrogenated, if desired. Oils derived from coal or shale may also be useful.

The major amount of base oil included in the gear fluids herein may be selected from the group consisting of Group I, Group II, a Group III, and a combination of two or more of the foregoing, and wherein the major amount of base oil is other than base oils that arise from provision of additive components or viscosity index improvers in the composition. In another embodiment, the major amount of base oil included in a lubricating composition may be selected from the group consisting of Group I, a Group II, and a combination of two or more of the foregoing, and wherein the major amount of base oil is other than base oils that arise from provision of additive components or viscosity index improvers in the composition.

The base oil may also be any of the synthetic base oils. Useful synthetic lubricating oils may include hydrocarbon oils such as polymerized, oligomerized, or interpolymerized olefins (e.g., polybutylenes, polypropylenes, propyleneisobutylene copolymers); poly(1-hexenes), poly(1-octenes), trimers or oligomers of 1-decene, e.g., poly(1-decenes), such materials being often referred to as α-olefins, and mixtures thereof; alkyl-benzenes (e.g. dodecylbenzenes, tetradecylbenzenes, dinonylbenzenes, di-(2-ethylhexyl)-benzenes); polyphenyls (e.g., biphenyls, terphenyls, alkylated polyphenyls); diphenyl alkanes, alkylated diphenyl alkanes, alkylated diphenyl ethers and alkylated diphenyl sulfides and the derivatives, analogs and homologs thereof or mixtures thereof. Polyalphaolefins are typically hydrogenated materials.

Other synthetic lubricating oils include polyol esters, diesters, liquid esters of phosphorus-containing acids (e.g., tricresyl phosphate, trioctyl phosphate, and the diethyl ester of decane phosphonic acid), or polymeric tetrahydrofurans. Synthetic oils may be produced by Fischer-Tropsch reactions and typically may be hydroisomerized Fischer-Tropsch hydrocarbons or waxes. In one embodiment oils may be prepared by a Fischer-Tropsch gas-to-liquid synthetic procedure as well as other gas-to-liquid oils.

The amount of the base oil of lubricating viscosity in the compositions herein may be the balance remaining after subtracting from 100 wt % the sum of the amount of the performance additives. For example, the oil of lubricating viscosity that may be present in a finished fluid may be a "major amount," such as greater than about 50 wt %, greater than about 60 wt %, greater than about 70 wt %, greater than about 80 wt %, greater than about 85 wt %, greater than about 90 wt %, or greater than about 95 wt %.

In some approaches, a preferred base oil or base oil of lubricating viscosity has less than about 25 ppm sulfur, a viscosity index greater than about 120 ppm, and a kinematic viscosity at about 100° C. of about 2 to about 8 cSt. In other approaches, the base oil of lubricating viscosity has less than about 25 ppm sulfur, a viscosity index greater than 120, and a kinematic viscosity at 100° C. of about 4 cSt. The base oil may have CP (paraffinic carbon content) of greater than 40%, greater than 45%, greater than 50%, greater than 55%, or greater than 90%. The base oil may have a CA (aromatic carbon content) of less than 5%, less than 3%, or less than 1%. The base oil may have a CN (naphthenic carbon content) of less than 60%, less than 55%, less than 50%, or less than 50% and greater than 30%. The base oil may have a ratio of 1 ring naphthenes to 2-6 ring naphthenes of less than 2 or less than 1.5 or less than 1.

A suitable driveline, transmission, or gear lubricant composition herein may include additive components in the ranges listed in the following Table 2.

TABLE 2

Suitable and Preferred Driveline or Gear Fluid Compositions

| Component | wt % (Suitable Embodiments) | wt % (Other Embodiments) |
|---|---|---|
| Corrosion Inhibitor | 0.05-0.2 | 0.1-0.15 |
| Phosphonate Diester (i.e., DMOP) | 0.1-0.5 | 0.2-0.3 |
| Antioxidant(s) | 0.1-5.0 | 0.01-4.0 |
| Detergent(s) | 0.0-15.0 | 1.0-8.0 |
| Corrosion inhibitor(s) | 0.0-5.0 | 0.1-3.0 |
| Ash-free phosphorus compound(s) | 0.0-15.0 | 0.1-5.0 |
| Antifoaming agent(s) | 0.0-1.0 | 0.001-0.5 |
| Antiwear agent(s) | 0.0-1.0 | 0.0-0.8 |
| Pour point depressant(s) | 0.0-1.0 | 0.01-0.5 |
| Viscosity index improver(s) | 0.0-20.0 | 0.1-10.0 |
| Dispersants | 0.0-10.0 | 1.0-6.0 |
| Dispersant viscosity index improver(s) | 0.0-10.0 | 0.0-5.0 |
| Friction modifier(s) | 0.0-10.0 | 0.01-4.0 |
| Extreme Pressure Agent | 0.0-1.05 | 0.035-0.35 |
| Base oil(s) | Balance | Balance |
| Total | 100 | 100 |

The percentages of each component above represent the weight percent of each component, based upon the weight of the total final additive or lubricating oil composition. The balance of the lubricating oil composition consists of one or more base oils or solvents. Additives used in formulating the compositions described herein may be blended into the base oil or solvent individually or in various sub-combinations. However, it may be suitable to blend all of the components concurrently using an additive concentrate (i.e., additives plus a diluent, such as a hydrocarbon solvent).

The lubricating composition described herein may be formulated to provide lubrication, enhanced friction performance properties, and improved copper corrosion for various applications. The driveline lubricating compositions herein may be used for lubricating a machine part, such as a gear. Lubricating fluids according to the present disclosure can be used in gear applications, such as industrial gear applications, automotive gear applications, axles, and stationary gearboxes. Gear-types can include, but are not limited to, spur, spiral, worm, rack and pinion, involute, bevel, helical, planetary, and hypoid gears and as well as limited-slip applications and differentials. The driveline lubricating compositions disclosed herein are also suitable for automatic or manual transmissions, including step automatic transmissions, continuously variable transmissions, semi-automatic transmissions, automated manual transmissions, toroidal transmissions, and dual clutch transmissions. The driveline lubricating compositions herein are particularly suited for use in axles, transfer cases, differentials, such as straight differentials, turning differentials, limited-slip differentials, clutch-type differentials, and locking differentials, and the like.

Optional Additives

In other approaches, the lubricant including such additives noted above may also include one or more optional components so long as such components and amounts thereof do not impact the performance characteristics as described in the above paragraphs. These optional components are described in the following paragraphs.

Phosphorus-Containing Compounds

The lubricant composition herein may comprise one or more phosphorus-containing compounds that may impart anti-wear benefits to the fluid. The one or more phosphorus-containing compounds may be present in the lubricating oil composition in an amount ranging from about 0 wt % to about 15 wt %, or about 0.01 wt % to about 10 wt %, or about 0.05 wt % to about 5 wt %, or about 0.1 wt % to about 3 wt % of the lubricating oil composition. The phosphorus-containing compound may provide up to 5000 ppm phosphorus, or from about 50 to about 5000 ppm phosphorus, or from about 300 to about 1500 ppm phosphorus, or up to 600 ppm phosphorus, or up to 900 ppm phosphorus to the lubricant composition.

The one or more phosphorus-containing compounds may include ashless phosphorus-containing compounds. Examples of suitable phosphorus-containing compound include, but are not limited to, thiophosphates, dithiophosphates, phosphates, phosphoric acid esters, phosphate esters, phosphites, phosphonates, phosphorus-containing carboxylic esters, ethers, or amides salts thereof, and mixtures thereof. Phosphorus containing anti-wear agents are more fully described in European Patent 0612839.

It should be noted that often the term phosphonate and phosphite are used often interchangeably in the lubricant industry. For example, dibutyl hydrogen phosphonate is often referred to as dibutyl hydrogen phosphite. It is within the scope of the present invention for the inventive lubricant composition to include a phosphorus-containing compound that may be referred to as either a phosphite or a phosphonate.

In any of the above described phosphorus-containing compounds, the compound may have about 5 to about 20 weight percent phosphorus, or about 5 to about 15 weight percent phosphorus, or about 8 to about 16 weight percent phosphorus, or about 6 to about 9 weight percent phosphorus.

The inclusion of the phosphorus-containing compound in combination with the above described dispersant to a lubricant compositions unexpectedly imparts positive frictional characteristics, such as a low friction coefficient, to the lubricant composition. The inventive effect is even further pronounced in some cases where the phosphorus-containing compound, on its own, imparts negative frictional characteristics to the fluid. When these relatively poor friction reducing phosphorus-containing compounds are combined with the olefin copolymer dispersant described herein, the lubricant composition has an improved, i.e., lower, friction coefficient. That is, the dispersants herein tend to transform fluids containing phosphorus-containing compounds having relatively poor friction coefficients into fluids with improved frictional properties.

This improvement in frictional properties of the lubricating compositions including the phosphorus-containing compounds and the olefin copolymer dispersant described herein is surprising because the frictional properties of the fluid are better than combinations of the phosphorus-containing compounds in combination with other types of dispersants, including polyisobutylene succinimide dispersants and olefin copolymer succinimide dispersants that do not have the specified characteristics of the copolymers described above.

Another type of phosphorus-containing compound that when combined with the olefin copolymer dispersant herein imparts improved frictional characteristics to a lubricating composition is an ashless (metal free) phosphorus-containing compound.

In some embodiments, the ashless phosphorus-containing compound may be dialkyl dithiophosphate ester, amyl acid phosphate, diamyl acid phosphate, dibutyl hydrogen phosphonate, dimethyl octadecyl phosphonate, salts thereof, and mixtures thereof.

The ashless phosphorus-containing compound may be have the formula:

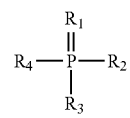

(Formula XIV)

wherein R1 is S or O; R2 is —OR, —OH, or —R"; R3 is —OR", —OH, or SR'"C(O)OH; R4 is —OR"; R'" is C1 to C3 branched or linear alkyl chain; and R" is a C1 to C18 hydrocarbyl chain. When the phosphorous-containing compound has the structure shown in Formula XIV, the compound may have about 8 to about 16 weight percent phosphorus.

In some embodiments the lubricant composition comprises a phosphorus-containing compound of Formula XIV wherein R1 is S; R2 is —OR"; R3 is S R'"COOH; R4 is —OR"; R'" is C3 branched alkyl chain; R" is C4; and wherein the phosphorus-containing compound is present in an amount to deliver between 80-900 ppm phosphorus to the lubricant composition.

In another embodiment, the lubricant composition comprises a phosphorus-containing compound of Formula XIV wherein R1 is O; R2 is —OH; R3 is —OR" or —OH; R4 is —OR"; R" is C5; and wherein phosphorus-containing compound is present in an amount to deliver between 80-1500 ppm phosphorus to the lubricant composition.

In yet another embodiment, the lubricant composition comprises a phosphorus-containing compound of Formula XIV wherein R1 is O; R2 is OR"; R3 is H; R4 is —OR"; R" is C4; and wherein the one or more phosphorus-containing compound(s) is present in an amount to deliver between 80-1550 ppm phosphorus to the lubricant composition.

In other embodiments, the lubricant composition comprises a phosphorus-containing compound of Formula XIV wherein R1 is O; R2 is —R—"; R3 is —OCH3 or —OH; R4 is —OCH3; R" is C18; and wherein the one or more phosphorus-containing compound(s) is present in an amount to deliver between 80-850 ppm phosphorus to the lubricant composition.

In some embodiments, the phosphorus-containing compound has the structure shown in Formula XIV and delivers about 80 to about 4500 ppm phosphorus to the lubricant composition. In other embodiments, the phosphorus-containing compound is present in an amount to deliver between about 150 and about 1500 ppm phosphorus, or between about 300 and about 900 ppm phosphorus, or between about 800 to 1600 ppm phosphorus, or about 900 to about 1800 ppm phosphorus, to the lubricant composition.

Anti-Wear Agents

The lubricant composition may also include other anti-wear agents that are non-phosphorus-containing compounds. Examples of such antiwear agents include borate esters, borate epoxides, thiocarbamate compounds (including thiocarbamate esters, alkylene-coupled thiocarbamates, and bis(S-alkyldithiocarbamyl)disulfides, thiocarbamate amides, thiocarbamic ethers, alkylene-coupled thiocarbamates, and bis(S-alkyldithiocarbamyl) disulfides, and mixtures thereof), sulfurized olefins, tridecyl adipate, titanium compounds, and long chain derivatives of hydroxyl carboxylic acids, such as tartrate derivatives, tartramides, tartrimides, citrates, and mixtures thereof. A suitable thiocarbamate compound is molybdenum dithiocarbamate. Suitable tartrate derivatives or tartrimides may contain alkyl-ester groups, where the sum of carbon atoms on the alkyl groups may be at least 8. The tartrate derivative or tartrimide may contain alkyl-ester groups, where the sum of carbon atoms on the alkyl groups may be at least 8. The antiwear agent may in one embodiment include a citrate. The additional anti-wear agent may be present in ranges including about 0 wt % to about 15 wt %, or about 0.01 wt % to about 10 wt %, or about 0.05 wt % to about 5 wt %, or about 0.1 wt % to about 3 wt % of the lubricating oil composition.

Extreme Pressure Agents

The lubricant compositions of the disclosure may also contain other extreme pressure agent(s) so long as the lubricating compositions herein include the noted amounts and profiles set forth herein. The optional extreme pressure agent may contain sulfur and may contain at least 12 percent by weight sulfur. In some embodiments, the extreme pressure agent added to the lubricating oil is sufficient to provide at least 350 ppm sulfur, 500 ppm sulfur, 760 ppm sulfur, from about 350 to about 2,000 ppm sulfur, from about 2,000 to about 30,000 ppm sulfur, or from about 2,000 to about 4,800 ppm sulfur, or about 4,000 to about 25,000 ppm sulfur to the lubricant composition.

A wide variety of sulfur-containing extreme pressure agents are suitable and include sulfurized animal or vegetable fats or oils, sulfurized animal or vegetable fatty acid esters, fully or partially esterified esters of trivalent or pentavalent acids of phosphorus, sulfurized olefins (see, for example U.S. Pat. Nos. 2,995,569; 3,673,090; 3,703,504; 3,703,505; 3,796,661; 3,873,454 4,119,549; 4,119,550; 4,147,640; 4,191,659; 4,240,958; 4,344,854; 4,472,306; and 4,711,736), dihydrocarbyl polysulfides (see for example U.S. Pat. Nos. 2,237,625; 2,237,627; 2,527,948; 2,695,316; 3,022,351; 3,308,166; 3,392,201; 4,564,709; and British 1,162,334), functionally-substituted dihydrocarbyl polysulfides (see for example U.S. Pat. No. 4,218,332), and polysulfide olefin products (see for example U.S. Pat. No. 4,795,576). Other suitable examples include organo-sulfur compounds selected from sulfurized olefins, sulfur-containing amino heterocyclic compounds, 5-dimercapto-1,3,4-thiadiazole, polysulfides having a majority of S3 and S4 sulfides, sulfurized fatty acids, sulfurized branched olefins, organic polysulfides, and mixtures thereof.

In some embodiments the extreme pressure agent is present in the lubricating composition in an amount of up to about 3.0 wt % or up to about 5.0 wt %. In other embodiments, the extreme pressure agent is present from about 0.05 wt % to about 0.5 wt %, based on the total lubricant composition. In other embodiments, the extreme pressure agent is present from about 0.1 wt % to about 3.0 wt %, based on the total lubricant composition. In other embodiments the extreme pressure agent is present in an amount between about 0.6 wt % and about 1 wt %, based on the total lubricant composition. In yet other embodiments, the detergent is present in an amount of about 1.0 wt %, based on the total lubricant composition.

One suitable class of extreme pressure agents are polysulfides composed of one or more compounds represented by the formula: Ra-Sx-Rb where Ra and Rb are hydrocarbyl groups each of which may contain 1 to 18, and in other approaches, 3 to 18 carbon atoms and x is may be in the range of from 2 to 8, and typically in the range of from 2 to 5, especially 3. In some approaches, x is an integer from 3 to 5 with about 30 to about 60 percent of x being an integer of 3 or 4. The hydrocarbyl groups can be of widely varying types such as alkyl, cycloalkyl, alkenyl, aryl, or aralkyl. Tertiary alkyl polysulfides such as di-tert-butyl trisulfide, and mixtures comprising di-tert-butyl trisulfide (e.g., a mixture composed principally or entirely of the tri, tetra-, and pentasulfides) may be used. Examples of other useful dihydrocarbyl polysulfides include the diamyl polysulfides, the dinonyl polysulfides, the didodecyl polysulfides, and the dibenzyl polysulfides.

Another suitable class of extreme pressure agent is sulfurized isobutenes made by reacting an olefin, such as isobutene, with sulfur. Sulfurized isobutene (SIB), notably sulfurized polyisobutylene, typically has a sulfur content of from about 10 to about 55%, desirably from about 30 to about 50% by weight. A wide variety of other olefins or unsaturated hydrocarbons, e.g., isobutene dimer or trimer, may be used to form the sulfurized olefin extreme pressure agents. Various methods have been disclosed in the prior art for the preparation of sulfurized olefins. See, for example, U.S. Pat. No. 3,471,404 to Myers; U.S. Pat. No. 4,204,969 to Papay et al.; U.S. Pat. No. 4,954,274 to Zaweski et al.; U.S. Pat. No. 4,966,720 to DeGonia et al.; and U.S. Pat. No. 3,703,504 to Horodysky, et al, each of which his incorporated herein by reference.

Methods for preparing sulfurized olefins, including the methods disclosed in the aforementioned patents, generally involve formation of a material, typically referred to as an adduct", in which an olefin is reacted with a sulfur halide, for example, sulfur monochloride. The adduct is then reacted with a sulfur source to provide the sulfurized olefin. The quality of a sulfurized olefin is generally measured by various physical properties, including, for example, viscosity, sulfur content, halogen content and copper corrosion test weight loss. U.S. Pat. No. 4,966,720, relates to sulfurized olefins useful as extreme pressure additives in lubrication oils and to a two stage reaction for their preparation.

Antioxidants

The lubricating oil compositions herein also may optionally contain one or more antioxidants. Antioxidant compounds are known and include for example, phenates, phenate sulfides, sulfurized olefins, phosphosulfurized terpenes, sulfurized esters, aromatic amines, alkylated diphenylamines (e.g., nonyl diphenylamine, di-nonyl diphenylamine, octyl diphenylamine, di-octyl diphenylamine), phenyl-alpha-naphthylamines, alkylated phenyl-alpha-naphthylamines, hindered non-aromatic amines, phenols, hindered phenols, oil-soluble molybdenum compounds, macromolecular antioxidants, or mixtures thereof. Antioxidant compounds may be used alone or in combination.

The hindered phenol antioxidant may contain a secondary butyl and/or a tertiary butyl group as a sterically hindering group. The phenol group may be further substituted with a hydrocarbyl group and/or a bridging group linking to a second aromatic group. Examples of suitable hindered phenol antioxidants include 2,6-di-tert-butylphenol, 4-methyl-2,6-di-tert-butylphenol, 4-ethyl-2,6-di-tert-butylphenol, 4-propyl-2,6-di-tert-butylphenol or 4-butyl-2,6-di-tert-butylphenol, or 4-dodecyl-2,6-di-tert-butylphenol. In one embodiment the hindered phenol antioxidant may be an ester and may include, e.g., Irganox® L-135 available from BASF or an addition product derived from 2,6-di-tert-butylphenol and an alkyl acrylate, wherein the alkyl group may contain about 1 to about 18, or about 2 to about 12, or about 2 to about 8, or about 2 to about 6, or about 4 carbon atoms. Another commercially available hindered phenol antioxidant may be an ester and may include Ethanox® 4716 available from Albemarle Corporation.

Useful antioxidants may include diarylamines and phenols. In an embodiment, the lubricating oil composition may contain a mixture of a diarylamine and a phenol, such that each antioxidant may be present in an amount sufficient to provide up to about 5 wt %, based on the weight of the lubricant composition. In an embodiment, the antioxidant may be a mixture of about 0.3 wt % to about 1.5 wt % diarylamine and about 0.4 wt % to about 2.5 wt % phenol, based on the lubricant composition.

Examples of suitable olefins that may be sulfurized to form a sulfurized olefin include propylene, butylene, isobutylene, polyisobutylene, pentene, hexene, heptene, octene, nonene, decene, undecene, dodecene, tridecene, tetradecene, pentadecene, hexadecene, heptadecene, octadecene, nonadecene, eicosene or mixtures thereof. In one embodiment, hexadecene, heptadecene, octadecene, nonadecene, eicosene or mixtures thereof and their dimers, trimers and tetramers are especially useful olefins. Alternatively, the olefin may be a Diels-Alder adduct of a diene such as 1,3-butadiene and an unsaturated ester, such as, butylacrylate.

Another class of sulfurized olefin includes sulfurized fatty acids and their esters. The fatty acids are often obtained from vegetable oil or animal oil and typically contain about 4 to about 22 carbon atoms. Examples of suitable fatty acids and their esters include triglycerides, oleic acid, linoleic acid, palmitoleic acid or mixtures thereof. Often, the fatty acids are obtained from lard oil, tall oil, peanut oil, soybean oil, cottonseed oil, sunflower seed oil or mixtures thereof. Fatty acids and/or ester may be mixed with olefins, such as α-olefins.

The one or more antioxidant(s) may be present in ranges about 0 wt % to about 20 wt %, or about 0.1 wt % to about 10 wt %, or about 1 wt % to about 5 wt %, of the lubricating oil composition.

Dispersants

Dispersants contained in the lubricant composition may include, but are not limited to, an oil soluble polymeric hydrocarbon backbone having functional groups that are capable of associating with particles to be dispersed. Typically, the dispersants comprise amine, alcohol, amide, or ester polar moieties attached to the polymer backbone often via a bridging group. Dispersants may be selected from Mannich dispersants as described in U.S. Pat. Nos. 3,634,515, 3,697,574 and 3,736,357; ashless succinimide dispersants as described in U.S. Pat. Nos. 4,234,435 and 4,636,322; amine dispersants as described in U.S. Pat. Nos. 3,219,666, 3,565,804, and 5,633,326; Koch dispersants as described in U.S. Pat. Nos. 5,936,041, 5,643,859, and 5,627,259, and polyalkylene succinimide dispersants as described in U.S. Pat. Nos. 5,851,965; 5,853,434; and 5,792,729.

In some embodiments, the additional dispersant may be derived from a polyalphaolefin (PAO) succinic anhydride, an olefin maleic anhydride copolymer. As an example, the additional dispersant may be described as a poly-PIBSA. In another embodiment, the additional dispersant may be derived from an anhydride which is grafted to an ethylene-propylene copolymer. Another additional dispersant may be a high molecular weight ester or half ester amide.

Dispersants are often known as ashless-type dispersants because, prior to mixing in a lubricating oil composition, they do not contain ash-forming metals and they do not normally contribute any ash when added to a lubricant. Ashless type dispersants are characterized by a polar group attached to a relatively high molecular weight hydrocarbon chain. Typical ashless dispersants include N-substituted long chain alkenyl succinimides. Examples of N-substituted long chain alkenyl succinimides include polyisobutylene succinimide with the number average molecular weight of the polyisobutylene substituent being in the range about 350 to about 50,000, or to about 5,000, or to about 3,000, as measured by GPC. Succinimide dispersants and their preparation are disclosed, for instance in U.S. Pat. No. 7,897,696 or U.S. Pat. No. 4,234,435. The alkenyl substituent may be prepared from polymerizable monomers containing about 2 to about 16, or about 2 to about 8, or about 2 to about 6 carbon atoms. Succinimide dispersants are typically the imide formed from a polyamine, typically a poly(ethyleneamine).

Preferred amines are selected from polyamines and hydroxyamines. Examples of polyamines that may be used include, but are not limited to, diethylene triamine (DETA), triethylene tetramine (TETA), tetraethylene pentamine (TEPA), and higher homologues such as pentaethylamine hexamine (PEHA), and the like.

A suitable heavy polyamine is a mixture of polyalkylenepolyamines comprising small amounts of lower polyamine oligomers such as TEPA and PEHA (pentaethylene hexamine) but primarily oligomers with 6 or more nitrogen atoms, 2 or more primary amines per molecule, and more extensive branching than conventional polyamine mixtures. A heavy polyamine preferably includes polyamine oligomers containing 7 or more nitrogens per molecule and with 2 or more primary amines per molecule. The heavy polyamine comprises more than 28 wt. % (e.g. >32 wt. %) total nitrogen and an equivalent weight of primary amine groups of 120-160 grams per equivalent.

In some approaches, suitable polyamines are commonly known as PAM and contain a mixture of ethylene amines where TEPA and pentaethylene hexamine (PEHA) are the major part of the polyamine, usually less than about 80%.

Typically, PAM has 8.7-8.9 milliequivalents of primary amine per gram (an equivalent weight of 115 to 112 grams per equivalent of primary amine) and a total nitrogen content of about 33-34 wt. %. Heavier cuts of PAM oligomers with practically no TEPA and only very small amounts of PEHA but containing primarily oligomers with more than 6 nitrogens and more extensive branching, may produce dispersants with improved dispersancy.

In an embodiment the present disclosure further comprises at least one polyisobutylene succinimide dispersant derived from polyisobutylene with a number average molecular weight in the range about 350 to about 50,000, or to about 5000, or to about 3000, as determined by GPC. The polyisobutylene succinimide may be used alone or in combination with other dispersants.

In some embodiments, polyisobutylene, when included, may have greater than 50 mol %, greater than 60 mol %, greater than 70 mol %, greater than 80 mol %, or greater than 90 mol % content of terminal double bonds. Such PM is also referred to as highly reactive PIB ("HR-PIB"). HR-PIB having a number average molecular weight ranging from about 800 to about 5000, as determined by GPC, is suitable for use in embodiments of the present disclosure. Conventional PM typically has less than 50 mol %, less than 40 mol %, less than 30 mol %, less than 20 mol %, or less than 10 mol % content of terminal double bonds.

An HR-PIB having a number average molecular weight ranging from about 900 to about 3000 may be suitable, as determined by GPC. Such HR-PIB is commercially available, or can be synthesized by the polymerization of isobutene in the presence of a non-chlorinated catalyst such as boron trifluoride, as described in U.S. Pat. No. 4,152,499 to Boerzel, et al. and U.S. Pat. No. 5,739,355 to Gateau, et al. When used in the aforementioned thermal ene reaction, HR-PIB may lead to higher conversion rates in the reaction, as well as lower amounts of sediment formation, due to increased reactivity. A suitable method is described in U.S. Pat. No. 7,897,696.

In one embodiment, the present disclosure further comprises at least one dispersant derived from polyisobutylene succinic anhydride ("PIBSA"). The PIBSA may have an average of between about 1.0 and about 2.0 succinic acid moieties per polymer.

The % actives of the alkenyl or alkyl succinic anhydride can be determined using a chromatographic technique. This method is described in column 5 and 6 in U.S. Pat. No. 5,334,321. The percent conversion of the polyolefin is calculated from the % actives using the equation in column 5 and 6 in U.S. Pat. No. 5,334,321.

In one embodiment, the dispersant may be derived from a polyalphaolefin (PAO) succinic anhydride. In one embodiment, the dispersant may be derived from olefin maleic anhydride copolymer. As an example, the dispersant may be described as a poly-PIBSA. In an embodiment, the dispersant may be derived from an anhydride which is grafted to an ethylene-propylene copolymer.

A suitable class of nitrogen-containing dispersants may be derived from olefin copolymers (OCP), more specifically, ethylene-propylene dispersants which may be grafted with maleic anhydride. A more complete list of nitrogen-containing compounds that can be reacted with the functionalized OCP are described in U.S. Pat. Nos. 7,485,603; 7,786,057; 7,253,231; 6,107,257; and 5,075,383; and/or are commercially available.

One class of suitable dispersants may also be Mannich bases. Mannich bases are materials that are formed by the condensation of a higher molecular weight, alkyl substituted phenol, a polyalkylene polyamine, and an aldehyde such as formaldehyde. Mannich bases are described in more detail in U.S. Pat. No. 3,634,515.

A suitable class of dispersants may also be high molecular weight esters or half ester amides. A suitable dispersant may also be post-treated by conventional methods by a reaction with any of a variety of agents. Among these are boron, urea, thiourea, dimercaptothiadiazoles, carbon disulfide, aldehydes, ketones, carboxylic acids, hydrocarbon-substituted succinic anhydrides, maleic anhydride, nitriles, epoxides, carbonates, cyclic carbonates, hindered phenolic esters, and phosphorus compounds. U.S. Pat. Nos. 7,645,726; 7,214,649; and 8,048,831 are incorporated herein by reference in their entireties.

In addition to the carbonate and boric acids post-treatments both the compounds may be post-treated, or further post-treatment, with a variety of post-treatments designed to improve or impart different properties. Such post-treatments include those summarized in columns 27-29 of U.S. Pat. No. 5,241,003, hereby incorporated by reference. Such treatments include, treatment with: Inorganic phosphorous acids or anhydrates (e.g., U.S. Pat. Nos. 3,403,102 and 4,648,980); Organic phosphorous compounds (e.g., U.S. Pat. No. 3,502,677); Phosphorous pentasulfides; Boron compounds as already noted above (e.g., U.S. Pat. Nos. 3,178,663 and 4,652,387); Carboxylic acid, polycarboxylic acids, anhydrides and/or acid halides (e.g., U.S. Pat. Nos. 3,708,522 and 4,948,386); Epoxides polyepoxiates or thioexpoxides (e.g., U.S. Pat. Nos. 3,859,318 and 5,026,495); Aldehyde or ketone (e.g., U.S. Pat. No. 3,458,530); Carbon disulfide (e.g., U.S. Pat. No. 3,256,185); Glycidol (e.g., U.S. Pat. No. 4,617,137); Urea, thiourea or guanidine (e.g., U.S. Pat. Nos. 3,312,619; 3,865,813; and British Patent GB 1,065,595); Organic sulfonic acid (e.g., U.S. Pat. No. 3,189,544 and British Patent GB 2,140,811); Alkenyl cyanide (e.g., U.S. Pat. Nos. 3,278,550 and 3,366,569); Diketene (e.g., U.S. Pat. No. 3,546,243); A diisocyanate (e.g., U.S. Pat. No. 3,573,205); Alkane sultone (e.g., U.S. Pat. No. 3,749,695); 1,3-Dicarbonyl Compound (e.g., U.S. Pat. No. 4,579,675); Sulfate of alkoxylated alcohol or phenol (e.g., U.S. Pat. No. 3,954,639); Cyclic lactone (e.g., U.S. Pat. Nos. 4,617,138; 4,645,515; 4,668,246; 4,963,275; and 4,971,711); Cyclic carbonate or thiocarbonate linear monocarbonate or polycarbonate, or chloroformate (e.g., U.S. Pat. Nos. 4,612,132; 4,647,390; 4,648,886; 4,670,170); Nitrogen-containing carboxylic acid (e.g., U.S. Pat. No. 4,971,598 and British Patent GB 2,140,811); Hydroxy-protected chlorodicarbonyloxy compound (e.g., U.S. Pat. No. 4,614,522); Lactam, thiolactam, thiolactone or dithiolactone (e.g., U.S. Pat. Nos. 4,614,603 and 4,666,460); Cyclic carbonate or thiocarbonate, linear monocarbonate or polycarbonate, or chloroformate (e.g., U.S. Pat. Nos. 4,612,132; 4,647,390; 4,646,860; and 4,670,170); Nitrogen-containing carboxylic acid (e.g., U.S. Pat. No. 4,971,598 and British Patent GB 2,440,811); Hydroxy-protected chlorodicarbonyloxy compound (e.g., U.S. Pat. No. 4,614,522); Lactam, thiolactam, thiolactone or dithiolactone (e.g., U.S. Pat. Nos. 4,614,603, and 4,666,460); Cyclic carbamate, cyclic thiocarbamate or cyclic dithiocarbamate (e.g., U.S. Pat. Nos. 4,663,062 and 4,666,459); Hydroxyaliphatic carboxylic acid (e.g., U.S. Pat. Nos. 4,482,464; 4,521,318; 4,713,189); Oxidizing agent (e.g., U.S. Pat.

No. 4,379,064); Combination of phosphorus pentasulfide and a polyalkylene polyamine (e.g., U.S. Pat. No. 3,185,647); Combination of carboxylic acid or an aldehyde or ketone and sulfur or sulfur chloride (e.g., U.S. Pat. Nos. 3,390,086; 3,470,098); Combination of a hydrazine and carbon disulfide (e.g. U.S. Pat. No. 3,519,564); Combination of an aldehyde and a phenol (e.g., U.S. Pat. Nos. 3,649,229; 5,030,249; 5,039,307); Combination of an aldehyde and an O-diester of dithiophosphoric acid (e.g., U.S. Pat. No. 3,865,740); Combination of a hydroxyaliphatic carboxylic acid and a boric acid (e.g., U.S. Pat. No. 4,554,086); Combination of a hydroxyaliphatic carboxylic acid, then formaldehyde and a phenol (e.g., U.S. Pat. No. 4,636,322); Combination of a hydroxyaliphatic carboxylic acid and then an aliphatic dicarboxylic acid (e.g., U.S. Pat. No. 4,663,064); Combination of formaldehyde and a phenol and then glycolic acid (e.g., U.S. Pat. No. 4,699,724); Combination of a hydroxyaliphatic carboxylic acid or oxalic acid and then a diisocyanate (e.g. U.S. Pat. No. 4,713,191); Combination of inorganic acid or anhydride of phosphorus or a partial or total sulfur analog thereof and a boron compound (e.g., U.S. Pat. No. 4,857,214); Combination of an organic diacid then an unsaturated fatty acid and then a nitrosoaromatic amine optionally followed by a boron compound and then a glycolating agent (e.g., U.S. Pat. No. 4,973,412); Combination of an aldehyde and a triazole (e.g., U.S. Pat. No. 4,963,278); Combination of an aldehyde and a triazole then a boron compound (e.g., U.S. Pat. No. 4,981,492); Combination of cyclic lactone and a boron compound (e.g., U.S. Pat. Nos. 4,963,275 and 4,971,711). The above-mentioned patents are herein incorporated in their entireties.

The TBN of a suitable dispersant may be from about 10 to about 65 mg KOH/g dispersant, on an oil-free basis, which is comparable to about 5 to about 30 TBN if measured on a dispersant sample containing about 50% diluent oil. TBN is measured by the method of ASTM D2896.

In yet other embodiments, the optional dispersant additive may be a hydrocarbyl substituted succinamide or succinimide dispersant. In approaches, the hydrocarbyl substituted succinamide or succinimide dispersant may be derived from a hydrocarbyl substituted acylating agent reacted with a polyalkylene polyamine and wherein the hydrocarbyl substituent of the succinamide or the succinimide dispersant is a linear or branched hydrocarbyl group having a number average molecular weight of about 250 to about 5,000 as measured by GPC using polystyrene as a calibration reference.

In some approaches, the polyalkylene polyamine used to form the dispersant has the Formula

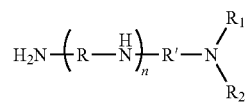

wherein each R and R', independently, is a divalent C1 to C6 alkylene linker, each $R_1$ and $R_2$, independently, is hydrogen, a C1 to C6 alkyl group, or together with the nitrogen atom to which they are attached form a 5- or 6-membered ring optionally fused with one or more aromatic or non-aromatic rings, and n is an integer from 0 to 8. In other approaches, the polyalkylene polyamine is selected from the group consisting of a mixture of polyethylene polyamines having an average of 5 to 7 nitrogen atoms, triethylenetetramine, tetraethylenepentamine, and combinations thereof.

The dispersant, if present, can be used in an amount sufficient to provide up to about 20 wt %, based upon the final weight of the lubricating oil composition. Another amount of the dispersant that can be used may be about 0.1 wt % to about 15 wt %, or about 0.1 wt % to about 10 wt %, about 0.1 to 8 wt %, or about 1 wt % to about 10 wt %, or about 1 wt % to about 8 wt %, or about 1 wt % to about 6 wt %, based upon the final weight of the lubricating oil composition. In some embodiments, the lubricating oil composition utilizes a mixed dispersant system. A single type or a mixture of two or more types of dispersants in any desired ratio may be used.

The dispersant, if present, can be used in an amount sufficient to provide up to about 10 wt %, based upon the final weight of the lubricating oil composition. Another amount of the dispersant that can be used may be about 0.1 wt % to about 10 wt %, or about 0.1 wt % to about 10 wt %, or about 3 wt % to about 8 wt %, or about 1 wt % to about 6 wt %, based upon the final weight of the lubricating oil composition.

Viscosity Index Improvers

The lubricant compositions herein also may optionally contain one or more viscosity index improvers. Suitable viscosity index improvers may include polyolefins, olefin copolymers, ethylene/propylene copolymers, polyisobutenes, hydrogenated styrene-isoprene polymers, styrene/maleic ester copolymers, hydrogenated styrene/butadiene copolymers, hydrogenated isoprene polymers, alpha-olefin maleic anhydride copolymers, polymethacrylates, polyacrylates, polyalkyl styrenes, hydrogenated alkenyl aryl conjugated diene copolymers, or mixtures thereof. Viscosity index improvers may include star polymers and suitable examples are described in US Publication No. 20120101017A1, which is incorporated herein by reference.

The lubricating oil compositions herein also may optionally contain one or more dispersant viscosity index improvers in addition to a viscosity index improver or in lieu of a viscosity index improver. Suitable viscosity index improvers may include functionalized polyolefins, for example, ethylene-propylene copolymers that have been functionalized with the reaction product of an acylating agent (such as maleic anhydride) and an amine; polymethacrylates functionalized with an amine, or esterified maleic anhydride-styrene copolymers reacted with an amine.

The total amount of viscosity index improver and/or dispersant viscosity index improver may be about 0 wt % to about 20 wt %, about 0.1 wt % to about 15 wt %, about 0.1 wt % to about 12 wt %, or about 0.5 wt % to about 10 wt %, about 3 wt % to about 20 wt %, about 3 wt % to about 15 wt %, about 5 wt % to about 15 wt %, or about 5 wt % to about 10 wt %, of the lubricating oil composition.

In some embodiments, the viscosity index improver is a polyolefin or olefin copolymer having a number average molecular weight of about 10,000 to about 500,000, about 50,000 to about 200,000, or about 50,000 to about 150,000. In some embodiments, the viscosity index improver is a hydrogenated styrene/butadiene copolymer having a number average molecular weight of about 40,000 to about 500,000, about 50,000 to about 200,000, or about 50,000 to about 150,000. In some embodiments, the viscosity index improver is a polymethacrylate having a number average molecular weight of about 10,000 to about 500,000, about 50,000 to about 200,000, or about 50,000 to about 150,000.

Other Optional Additives

Other additives may be selected to perform one or more functions required of lubricant composition. Further, one or more of the mentioned additives may be multi-functional and provide functions in addition to or other than the function prescribed herein. The other additives may be in addition to specified additives of the present disclosure and/or may comprise one or more of metal deactivators, viscosity index improvers, ashless TBN boosters, antiwear agents, corrosion inhibitors, rust inhibitors, dispersants, dispersant viscosity index improvers, extreme pressure agents, antioxidants, foam inhibitors, demulsifiers, emulsifiers, pour point depressants, seal swelling agents and mixtures thereof. Typically, fully-formulated lubricating oil will contain one or more of these additives.

Suitable metal deactivators may include derivatives of benzotriazoles (typically tolyltriazole), dimercaptothiadiazole derivatives, 1,2,4-triazoles, benzimidazoles, 2-alkyldithiobenzimidazoles, or 2-alkyldithiobenzothiazoles; foam inhibitors including copolymers of ethyl acrylate and 2-ethylhexylacrylate and optionally vinyl acetate; demulsifiers including trialkyl phosphates, polyethylene glycols, polyethylene oxides, polypropylene oxides and (ethylene oxide-propylene oxide) polymers; pour point depressants including esters of maleic anhydride-styrene, polymethacrylates, polyacrylates or polyacrylamides.

Suitable foam inhibitors include silicon-based compounds, such as siloxane.

Suitable pour point depressants may include a polymethylmethacrylates or mixtures thereof. Pour point depressants may be present in an amount sufficient to provide from about 0 wt % to about 1 wt %, about 0.01 wt % to about 0.5 wt %, or about 0.02 wt % to about 0.04 wt % based upon the final weight of the lubricating oil composition.

Suitable rust inhibitors may be a single compound or a mixture of compounds having the property of inhibiting corrosion of ferrous metal surfaces. Non-limiting examples of rust inhibitors useful herein include oil-soluble high molecular weight organic acids, such as 2-ethylhexanoic acid, lauric acid, myristic acid, palmitic acid, oleic acid, linoleic acid, linolenic acid, behenic acid, and cerotic acid, as well as oil-soluble polycarboxylic acids including dimer and trimer acids, such as those produced from tall oil fatty acids, oleic acid, and linoleic acid. Other suitable corrosion inhibitors include long-chain alpha, omega-dicarboxylic acids in the molecular weight range of about 600 to about 3000 and alkenylsuccinic acids in which the alkenyl group contains about 10 or more carbon atoms such as, tetrapropenylsuccinic acid, tetradecenylsuccinic acid, and hexadecenylsuccinic acid. Another useful type of acidic corrosion inhibitors are the half esters of alkenyl succinic acids having about 8 to about 24 carbon atoms in the alkenyl group with alcohols such as the polyglycols. The corresponding half amides of such alkenyl succinic acids are also useful. A useful rust inhibitor is a high molecular weight organic acid. In some embodiments, an engine oil is devoid of a rust inhibitor.

The rust inhibitor, if present, can be used in optional amount sufficient to provide about 0 wt % to about 5 wt %, about 0.01 wt % to about 3 wt %, about 0.1 wt % to about 2 wt %, based upon the final weight of the lubricating oil composition.

The lubricant composition may also include corrosion inhibitors (it should be noted that some of the other mentioned components may also have copper corrosion inhibition properties). Suitable inhibitors of copper corrosion include ether amines, polyethoxylated compounds such as ethoxylated amines and ethoxylated alcohols, imidazolines, monoalkyl and dialkyl thiadiazole, and the like.

Thiazoles, triazoles and thiadiazoles may also be used in the lubricants. Examples include benzotriazole, tolyltriazole, octyltriazole, decyltriazole; dodecyltriazole, 2-mercaptobenzothiazole, 2,5-dimercapto-1,3,4-thiadiazole, 2-mercapto-5-hydrocarbylthio-1,3,4-thiadiazoles, and 2-mercapto-5-hydrocarbyldithio-1,3,4-thiadiazoles. In one embodiment, the lubricant composition includes a 1,3,4-thiadiazole, such as 2-hydrocarbyldithio-5-mercapto-1,3,4-dithiadiazole.

Anti-foam/Surfactant agents may also be included in a fluid according to the present invention. Various agents are known for such use. Copolymers of ethyl acrylate and hexyl ethyl acrylate, such as PC-1244, available from Solutia may be used. In other embodiments, silicone fluids, such as 4% DCF may be included. Mixtures of anti-foam agents may also be present in the lubricant composition.

EXAMPLES

The following examples are illustrative of exemplary embodiments of the disclosure. In these examples, as well as elsewhere in this application, all ratios, parts, and percentages are by weight unless otherwise indicated. It is intended that these examples are being presented for the purpose of illustration only and are not intended to limit the scope of the invention disclosed herein.

Comparative Example 1

A comparative corrosion inhibitor including a mixture of dialkyl-thiadiazole compounds and monoalkyl-thiadiazole compounds was prepared as follows: a 2 liter kettle equipped with baffles, a condenser, and gas outlet connected to caustic/bleach scrubbers was charged with 43.3% aqueous sodium 2,5-dimercapto-1,3,4-thiadiazole (NaDMTD, 504.0 g, 1.267 moles), 98.7% tert-nonyl mercaptan (334.0 g, 2.059 moles), and 95% sulfuric acid (77.8 g, 0.75 moles). To this mixture was added 50% hydrogen peroxide (144.4 g, 2.123 moles) over 3 hours and 50 minutes at a temperature of about 75° C. to about 85° C. The reaction temperature was then increased to about 90° C. and a water layer separated off followed by a vacuum strip at a temperature of about 110° C. or less.

This reaction had 1.624 molar equivalents of the alkyl mercaptan relative to the thiadiazole and 1.675 molar equivalents of the hydrogen peroxide to the thiadiazole forming an overall reaction molar ratio of the thiadiazole to the mercaptan to the peroxide of 1:1.62:1.68. The sample had a total acid number (TAN) of about 30.6, and the final product contained a 74.3:25.4 molar ratio of dialkyl-thiadiazole to monoalkyl-thiadiazole as measured by C NMR.

Comparative Example 2

A comparative corrosion inhibitor was prepared as follows: a 2 liter kettle equipped with baffles, a condenser, and gas outlet connected to caustic/bleach scrubbers was charged with 43.3% sodium 2,5-dimercapto-1,3,4-thiadiazole (NaDMTD, 447.6 g, 1.125 moles), 98.7% tert-nonyl mercaptan (413.0 g, 2.546 moles), and 95% sulfuric acid (70.5 g, 0.68 moles). To this mixture 50% hydrogen peroxide (198.0 g, 2.912 moles) was added. The reaction temperature was then increased to about 90° C. and a water layer separated off followed by a vacuum strip at a temperature of about 110° C. or less.

This reaction had 2.262 molar equivalents of the alkyl mercaptan relative to the thiadiazole and 2.587 molar equivalents of the hydrogen peroxide to the thiadiazole forming an overall reaction molar ratio of the thiadiazole to the mercaptan to the peroxide of 1:2.26:2.59. The sample had a total acid number (TAN) of about 22, and the final product had a molar ratio of dialkyl-thiadiazole to monoalkyl-thiadiazole as measured by C NMR of greater than 91:9.

Example 1

An inventive corrosion inhibitor primarily including dialkyl-thiadiazole compounds was prepared as follows: a 2 liter kettle equipped with baffles, a condenser, and gas outlet connected to caustic/bleach scrubbers was charged with 43.3% aqueous sodium 2,5-dimercapto-1,3,4-thiadiazole (NaDMTD, 447.6 g, 1.125 moles), 98.7% tert-nonyl mercaptan (386.0 g, 2.379 moles), and 95% sulfuric acid (69.1 g, 0.70 moles). To this mixture, 50% hydrogen peroxide (167.3 g, 2.460 moles) was added over 3 hours and 50 minutes at a temperature of about 75° C. to about 85° C. The reaction temperature was then increased to about 90° C. and a water layer separated off followed by a vacuum strip at a temperature of about 110° C. or less.

This reaction had 2.113 molar equivalents of the alkyl mercaptan relative to the thiadiazole and 2.186 molar equivalents of the hydrogen peroxide to the thiadiazole forming an overall reaction molar ratio of the thiadiazole to the mercaptan to the peroxide of 1:2.11:2.19. The sample had a total acid number (TAN) of about 8, and the final product had undetectable levels of monalkyl thiadiazole compounds with a molar ratio of dialkyl-thiadiazole to monoalkyl-thiadiazole as measured by C NMR of greater than 99:1.

Example 2

Another inventive corrosion inhibitor primarily including dialkyl-thiadiazole compounds was prepared as follows: a 2 liter kettle equipped with baffles, a condenser, and gas outlet connected to caustic/bleach scrubbers was charged with 43.3% aqueous sodium 2,5-dimercapto-1,3,4-thiadiazole (NaDMTD, 500 g, 1.257 moles), 98.7% tert-nonyl mercaptan (408.7 g, 2.519 moles), and 95% sulfuric acid (74.1 g, 0.72 moles). To this mixture was added 50% hydrogen peroxide (188.5 g, 2.772 moles) over 3 hours and 50 minutes at a temperature of about 75° C. to about 85° C. A sample was removed following the mercaptan/peroxide addition and a total acid number (TAN) of less than about 10 measured. The reaction temperature was increased to 90° C. and a water layer separated off followed by a vacuum strip at about 110° C. or less.

This reaction had 2.004 molar equivalents of the alkyl mercaptan relative to the thiadiazole and a peroxide factor of 2.205 molar equivalents of the hydrogen peroxide to the thiadiazole forming an overall reaction molar ratio of the thiadiazole to the mercaptan to the peroxide of 1:2.00:2.21. The sample had a total acid number (TAN) of about 8, and the final product had undetectable levels of monalkyl thiadiazole compounds with a molar ratio of dialkyl-thiadiazole to monoalkyl-thiadiazole as measured by C NMR of greater than 99:1.

Example 3

Another inventive corrosion inhibitor primarily including dialkyl-thiadiazole compounds was prepared as follows: a 2 liter kettle equipped with baffles, a condenser, and gas outlet connected to caustic/bleach scrubbers was charged with 43.3% aqueous sodium 2,5-dimercapto-1,3,4-thiadiazole (NaDMTD, 160 g, 0.402 moles), 98.7% tert-nonyl mercaptan (127.2 g, 0.874 moles), and 95% sulfuric acid (23.5 g, 0.228 moles). To this mixture was added 50% hydrogen peroxide (59.8 g, 0.879 moles) over 3 hours and 50 minutes at a temperature of about 75° C. to about 85° C. A sample was removed following the mercaptan/peroxide addition and a total acid number (TAN) of less than about 10 measured. The reaction temperature was increased to 90° C. and a water layer separated off followed by a vacuum strip at about 110° C. or less.

This reaction had 1.949 molar equivalents of the alkyl mercaptan relative to the thiadiazole and 2.186 molar equivalents of the hydrogen peroxide to the thiadiazole forming an overall reaction molar ratio of the thiadiazole to the mercaptan to the peroxide of 1:1.95:2.19. The sample had a total acid number (TAN) of about 10, and the final product had undetectable levels of monalkyl thiadiazole compounds with a molar ratio of dialkyl-thiadiazole to monoalkyl-thiadiazole as measured by C NMR of greater than 99:1.

Example 4

The corrosion inhibitors of Comparative Example 1 and Example 1 were each formulated into a finished lubricant at a treat rate of 0.35 weight percent. The finished lubricants also included 0.25 weight percent of dimethyl octadecyl phosphonate (DMOP) and the same base additive package in a Group 4 base oil having a KV100 of 39.2 cSt.

The finished lubricants were thermally aged at about 40° C. or about 55° C. and evaluated for the presence of methyl octadecyl phosphonate (MOP). The graphs of FIGS. 1 and 2 show a marked improvement in DMOP stability for the finished lubricant including the inventive thiadiazole corrosion inhibitor of Example 1 as compared to the finished lubricant including the comparative thiadiazole corrosion inhibitor of Comparative Example 1.

The finished lubricants were also evaluated for copper corrosion pursuant to ASTM D130 at 121° C. after 3 hours, the relative ratio of DMOP to MOP after 8 weeks of storage at room temperature (25° C.), and FAG FE8 roller bearing weight loss was measured pursuant to DIN 51819-3 at 80 hours, 7.5 rpm, 100 kN, and 80° C. run conditions. Results are provided in Table 3 below.

TABLE 3

|  | Copper Corrosion Rating | DMOP:MOP molar ratio | FAG FE8 Roller Bearing Weight Loss, mg |
|---|---|---|---|
| Comparative Example 1 | 1B | 83:17 | 19 |
| Example 1 | 1B | 95:5 | 10 |

As shown in Table 3 above, finished lubricants including the inventive corrosion inhibitor of Example 1 had the same copper corrosion rating as a finished lubricant including the comparative corrosion inhibitor of Comparative Example 1, but the inventive lubricants and additives had a higher molar ratio of the phosphonate diester (DMOP) relative to the phosphonate monoester (MOP) and, as a result, a dramatically improved roller bearing weight loss. Similar results are expected with the lubricants of Examples 2 and 3 and Comparative Example 2.

It is noted that, as used in this specification and the appended claims, the singular forms "a," "an," and "the," include plural referents unless expressly and unequivocally limited to one referent. Thus, for example, reference to "an antioxidant" includes two or more different antioxidants. As used herein, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is to be understood that each component, compound, substituent or parameter disclosed herein is to be interpreted as being disclosed for use alone or in combination with one or more of each and every other component, compound, substituent or parameter disclosed herein.

It is further understood that each range disclosed herein is to be interpreted as a disclosure of each specific value within the disclosed range that has the same number of significant digits. Thus, for example, a range from 1 to 4 is to be interpreted as an express disclosure of the values 1, 2, 3 and 4 as well as any range of such values.

It is further understood that each lower limit of each range disclosed herein is to be interpreted as disclosed in combination with each upper limit of each range and each specific value within each range disclosed herein for the same component, compounds, substituent or parameter. Thus, this disclosure to be interpreted as a disclosure of all ranges derived by combining each lower limit of each range with each upper limit of each range or with each specific value within each range, or by combining each upper limit of each range with each specific value within each range. That is, it is also further understood that any range between the endpoint values within the broad range is also discussed herein. Thus, a range from 1 to 4 also means a range from 1 to 3, 1 to 2, 2 to 4, 2 to 3, and so forth.

Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A corrosion inhibitor made by a process comprising:
   (a) reacting a 1,3,4-dimercapto thiadiazole or alkali metal salt thereof with an alkyl mercaptan in the presence of an acid to form a first reaction intermediate;
   (b) reacting the first reaction intermediate with hydrogen peroxide to form the corrosion inhibitor; and
   (c) wherein the 1,3,4-dimercapto thiadiazole or alkali metal salt thereof, the alkyl mercaptan, and the hydrogen peroxide are provided at a molar ratio of 1:1.95-2.15:2.1-2.4.

2. The corrosion inhibitor of claim 1, wherein the acid is a strong acid provided in molar excess to the 1,3,4-dimercapto thiadiazole.

3. The corrosion inhibitor of claim 1, wherein the corrosion inhibitor is about 95 mol percent or more of a 2,5-dialkyl-dithiothiadiazole compound and about 5 mol percent or less of a monoalkyl-dithiothiadiazole compound.

4. The corrosion inhibitor of claim 1, wherein the corrosion inhibitor has a total acid number of 10 or less.

5. The corrosion inhibitor of claim 1, wherein the process further includes heating the corrosion inhibitor to a temperature effective to separate any aqueous layer and optionally subjecting the heated corrosion inhibitor to a vacuum strip.

6. The corrosion inhibitor of claim 3, wherein the 2,5-dialkyl-dithiothiadiazole compound has the structure of Formula Ia:

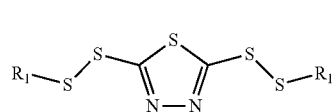

(Formula Ia)

and
wherein the monoalkyl-dithiothiadiazole compound has the structure of Formula Ib:

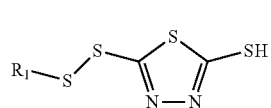

(Formula Ib)

wherein each $R_1$ of Formula Ia and/or Formula Ib is independently a linear or branched C4 to C20 hydrocarbyl group.

7. The corrosion inhibitor of claim 1, wherein the alkyl moiety of the alkyl mercaptan is an aliphatic or aromatic hydrocarbyl group.

8. The corrosion inhibitor of claim 7, wherein the alkyl moiety of the alkyl mercaptan is a linear or branched C1 to C30 hydrocarbyl group.

9. A lubricant comprising:
   (a) a majority of base oil; and
   (b) a corrosion inhibitor made by a process comprising:
      (i) reacting a 1,3,4-dimercapto thiadiazole or alkali metal salt thereof with an alkyl mercaptan in the presence of an acid to form a first reaction intermediate;
      (ii) reacting the first reaction intermediate with hydrogen peroxide to form the corrosion inhibitor; and
      (iii) wherein the 1,3,4-dimercapto thiadiazole or alkali metal salt thereof, the alkyl mercaptan, and the hydrogen peroxide are provided at a molar ratio of 1:1.95-2.15:2.1-2.4.

10. The lubricant of claim 9, wherein the acid is a strong acid provided in molar excess to the 1,3,4-dimercapto thiadiazole.

11. The lubricant of claim 9, further comprising one or more phosphonate ester compounds including, based on the total weight percent of phosphonate ester compounds, about 90 weight percent or more of a phosphonate diester and no more than about 10 weight percent of a phosphonate monoester.

12. The lubricant of claim 9, wherein the corrosion inhibitor is about 95 mol percent or more of a 2,5-dialkyl-dithiothiadiazole compound and about 5 mol percent or less of a monoalkyl-dithiothiadiazole compound.

13. The lubricant of claim 12, wherein the 2,5-dialkyl-dithiothiadiazole compound has the structure of Formula Ia:

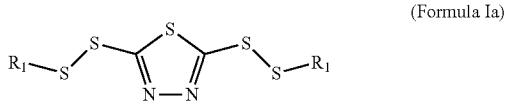

(Formula Ia)

and wherein the monoalkyl-dithiothiadiazole compound has the structure of Formula Ib:

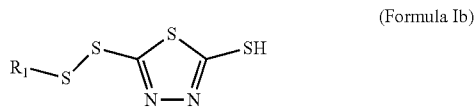

(Formula Ib)

wherein each $R_1$ of Formula Ia and/or Formula Ib is, independently, a linear or branched C4 to C20 hydrocarbyl group.

14. The lubricant of claim 11, wherein the phosphonate diester has a structure of Formula II

(Formula II)

wherein $R_2$ is a $C_1$ to $C_{50}$ hydrocarbyl group and each $R_3$ is, independently, a $C_1$ to $C_{20}$ alkyl group.

15. The lubricant of claim 14, wherein the phosphonate diester is dimethyl octadecyl phosphonate.

16. The lubricant of claim 11, wherein the phosphonate monoester has a structure of Formula III

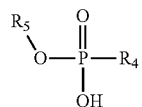

(Formula III)

wherein $R_4$ is a $C_1$ to $C_{50}$ hydrocarbyl group and $R_5$ is a $C_1$ to $C_{20}$ alkyl group.

17. The lubricant of claim 16, wherein the phosphonate monoester is methyl octadecyl phosphonate.

18. The lubricant of claim 9, wherein the process further includes heating the corrosion inhibitor to a temperature effective to separate any aqueous layer and optionally subjecting the heated corrosion inhibitor to a vacuum strip.

19. The lubricant of claim 9, wherein the lubricant exhibits a FAG FE8 roller bearing weight loss of about 12 mg of less pursuant to DIN 51819-3 after 80 hours of runtime at 80° C., 7.5 rpm, and 100 kN.

20. A corrosion inhibitor additive comprising:
(a) about 95 mol percent or more of a 2,5-dialkyl-dithiothiadiazole compound;
(b) a monoalkyl-dithiothiadiazole compound, but no more than about 5 mol percent of the monoalkyl-dithiothiadaizole compound; and
(c) wherein the total acid number of the corrosion inhibitor additive is about 10 or less; and
wherein the corrosion inhibitor is obtained from a dimercapto thiadiazole or alkali metal salt thereof, an alkyl mercaptan, and a hydrogen peroxide provided at a molar ratio of 1:1.95-2.15:2.1-2.4.

21. The corrosion inhibitor of claim 20, wherein the 2,5-dialkyl-dithiothiadiazole compound has the structure of Formula Ia:

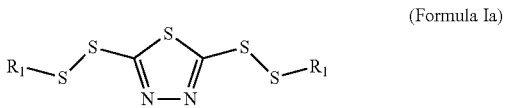

(Formula Ia)

and wherein the monoalkyl-dithiothiadiazole compound has the structure of Formula Ib:

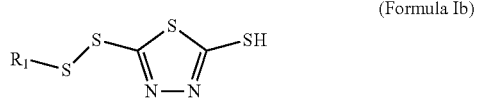

(Formula Ib)

wherein each $R_1$ of Formula Ia and/or Formula Ib is independently a linear or branched C4 to C20 hydrocarbyl group.

* * * * *